US00PP34041P2

(12) United States Plant Patent
Clark

(10) Patent No.: US PP34,041 P2
(45) Date of Patent: Mar. 15, 2022

(54) ***COLEUS* PLANT NAMED 'UF17-52-25'**

(50) Latin Name: *Coleus scutellarioides*
Varietal Denomination: UF17-52-25

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 17/300,454

(22) Filed: Jul. 6, 2021

(51) Int. Cl.
*A01H 5/12* (2018.01)
*A01H 6/50* (2018.01)

(52) U.S. Cl.
USPC ..... Plt./469

(58) Field of Classification Search
USPC ..... Plt./469
See application file for complete search history.

*Primary Examiner* — Susan McCormick Ewoldt
(74) *Attorney, Agent, or Firm* — Katherine Koenig; Koenig IP Works, PLLC

(57) ABSTRACT

'UF17-52-25' is a new *Coleus* plant, selected for having a combination of desirable traits that make it well-suited for good performance as an annual plant in the summer landscape. 'UF17-52-25' has foliage that is consistent burnt orange with pink mid-veins (in older leaves), surrounded by well-defined light green leaf margins and leaf undersides. This combination of colors and patterns makes it eye-catching. 'UF17-52-25' is exceptional because it maintains these colors in a broad range of environmental conditions, and it has received superior ratings in both our sun and shade trials. It is upright in growth habit, but it is more highly branched and uniform in shape than most ruffled-leaf-type plants that have been produced to date. This allows the plant to have high utility for use in any part of the garden landscape.

3 Drawing Sheets

Genus and species: *Coleus scutellarioides*.

Cultivar denomination: The present disclosure relates to *Coleus* cultivar 'UF17-52-25'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

*Coleus* (previously *Solenostemon scutellarioides* or *Plectranthus scutellarioides*, now *Coleus scutellarioides*) plants are used as annual bedding plants for the landscape and mixed containers in summer gardens. *Coleus* plants are popular for commercial growers and landscapers because they are easy to propagate and provide fast and reliable attractive foliage color that performs well at all points in the perishable garden plant supply chain. *Coleus* plants are also popular with home gardeners because they are easy to grow in both full sun and partial shade conditions, and require less maintenance than many other annual garden plants. From the breeder perspective, there is much genotypic variability in *Coleus* because it is a tetraploid with active transposons and there are a number of different visible phenotypes including foliage color, leaf shape and size, plant height, time to flowering, and growth habit.

The *Coleus* breeding program in Gainesville, Fla., was initiated in 2003 with an emphasis on developing new clonally propagated cultivars that are profitable for producers and perform well in consumer gardens with little or no care. Using recurrent mass selection and maintaining a large pool of germplasm our program has released over 85 new cultivars into the industry since 2007. The *Coleus* breeding program has focused on screening for new cultivars with novel leaf colors and shapes, increased vigor and branching, and late flowering, by conducting greenhouse and field trials under demanding environmental conditions. Greenhouse trials under "lush" conditions that push the plants to grow as fast as possible with high amounts of light, high fertility and high temperatures are used because these conditions allow for rapid discernment of growth habits and vigor characteristics, and also facilitate observation of plant phenotypes under conditions where greenhouse pathogen and insect pressure is highest. A first group of field trials in Citra, Fla., are planted in full sun in sand beds with plastic mulch in May-June each year with drip irrigation, minimal added fertilizer, and no chemical control for insects or pathogens. A second group of field trials in Citra, Fla., are planted in 30% shade in sand beds in May-June each year with drip irrigation and a minimal amount of slow-release fertilizer added at planting. These "lean" growing conditions are used in the field trials to screen for plants that grow vigorously and consistently for minimalist gardeners. *Coleus* produces a better seed crop under "lean" conditions than "lush" conditions, which is useful for making open-pollinated seeds. Since data is collected on a large number of genotypes (~600-800 per year), each trial only contains 1-3 plants per genotype. If a genotype performs poorly in any trial it is automatically discarded from the program, leaving ~200-250 genotypes in the program as elite stock at the end of each year.

Desirable characteristics that continue to be in demand a decade after first commercial introductions are: (1) foliage color stability in sun and shade; (2) consistent well-branched plant habit; and (3) late flowering. Improved plants with interesting foliage colors in both full sun and shade conditions allow for more versatile garden use and more color choices for gardeners. Superior well-branched plant habit is important throughout the production chain from the propagator/grower to the consumer, which allows for production of a large number of vegetative propagules and translates into more manageable plants for producers during culture and shipping to retail outlets. Once planted in the garden, these well-branched plants require less management over a long season of growth. Late flowering is a desirable characteristic because early flowering triggers senescence of the lower leaves and decreases foliage quality of *Coleus*. Floral induction often slows vegetative growth, and increases landscape maintenance with manual dead-heading and plant replacement, which is vital to landscape contractors. Late or 'no flowering' genotypes with good branching and stable foliage color that have been developed in Gainesville, Fla., have performed well in commercial markets, and continue to attract interest from US, European, and Asian gardeners. The plant disclosed herein was selected because it has many of these desirable traits.

SUMMARY OF THE INVENTION

The invention relates to a new and distinct cultivar of *Coleus* plant named 'UF17-52-25'. The new cultivar 'UF17-52-25' originated from an open pollination conducted in May-November 2016 in Gainesville, Fla., between the female *Coleus* plant 'UF16-39-4' (unpatented) and an unknown male *Coleus* plant. A single seedling was chosen in May 2017 for further asexual propagation in Gainesville, Fla.

The new cultivar 'UF17-52-25' has been reproduced asexually for over eighteen (18) months through vegetative cuttings and has been found to retain its distinctive characteristics through successive asexual propagations. 'UF17-52-25' was first propagated asexually by meristem tip cuttings in May, 2017, in Gainesville, Fla., and has remained true-to-type since that time.

The new *Coleus* cultivar 'UF17-52-25' has not been observed under all possible environmental conditions. The phenotype of the new cultivar may vary with variations in environmental and cultural practices such as temperature, light intensity, fertilization, irrigation, and application of plant growth regulators without any change in genotype.

Plant Breeder's Rights for 'UF17-52-25' have not been applied for. The new cultivar 'UF17-52-25' has not been made publicly available prior to the filing date of this application.

The new cultivar 'UF17-52-25' was selected because it has unique, highly lobed-shaped leaves with novel color, and because it has not been observed to produce flowers in any field or greenhouse trials. It performs well in sun and shade and has excellent vigor to withstand the harsh selection conditions our plants are subjected to in full sun trials in Gainesville, Fla. The new cultivar 'UF17-52-25' is exceptional because it maintains both distinct colors in well-defined zones in shade or sun.

The following are the most outstanding and distinguishing characteristics of the new cultivar 'UF17-52-25' when grown under normal horticultural practices in Gainesville, Fla.: the new cultivar 'UF17-52-25' has the combination of vigorous, upright growth habit, excellent heat tolerance, and consistent multi-colored leaves that are significantly different than other *Coleus* plants. The new cultivar 'UF17-52-25' is more highly branched and uniform in shape than most ruffled-leaf-type *Coleus* plants. It has superior stability in foliage color in both sun and shade conditions, maintaining stable color in all conditions. It has a compact form with excellent lateral branching, making it suitable for propagators and producers. The new cultivar 'UF17-52-25' has been observed to have long-season performance in landscape trials in Gainesville, Fla.

When compared to the female parent 'UF16-39-4', plants of the new *Coleus* cultivar 'UF17-52-25' have large leaves that are highly lobed. The upper (adaxial) leaf surface is burnt orange with well-defined light green margins, and these colors are accentuated in older leaves with a pink mid-vein. The lower (abaxial) leaf surface is uniformly colored light green, which accentuates the other colors on the adaxial leaf surface. In contrast, plants of 'UF16-39-4' have smaller leaves colored dark maroon with green margins that are only slightly lobed in shape. The new cultivar 'UF17-52-25' has a vigorous compact form and a upright, well-branched growth habit, whereas 'UF16-39-4' is much less vigorous, and more spreading in form with less lateral branching.

DESCRIPTION OF THE FIGURES

The accompanying photographs (as shown in FIGS. 1-3) illustrate the overall appearance of the new *Coleus* cultivar 'UF17-52-25'. These photographs show the colors as true as can be reasonably obtained by conventional photographic procedures. Colors shown in the photographs may differ slightly from the color values cited in the detailed botanical description, which accurately describe the colors of the new *Coleus* cultivar.

FIG. 2 shows the growth habit, form, and foliage of the claimed plant; and

FIG. 3 shows a close-up of the foliage of the claimed plant.

DETAILED BOTANICAL DESCRIPTION OF THE CULTIVAR

Figure 1:
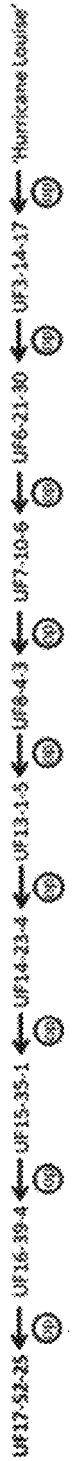
FIG. 1 shows the pedigree of the claimed plant.
Figure 2:
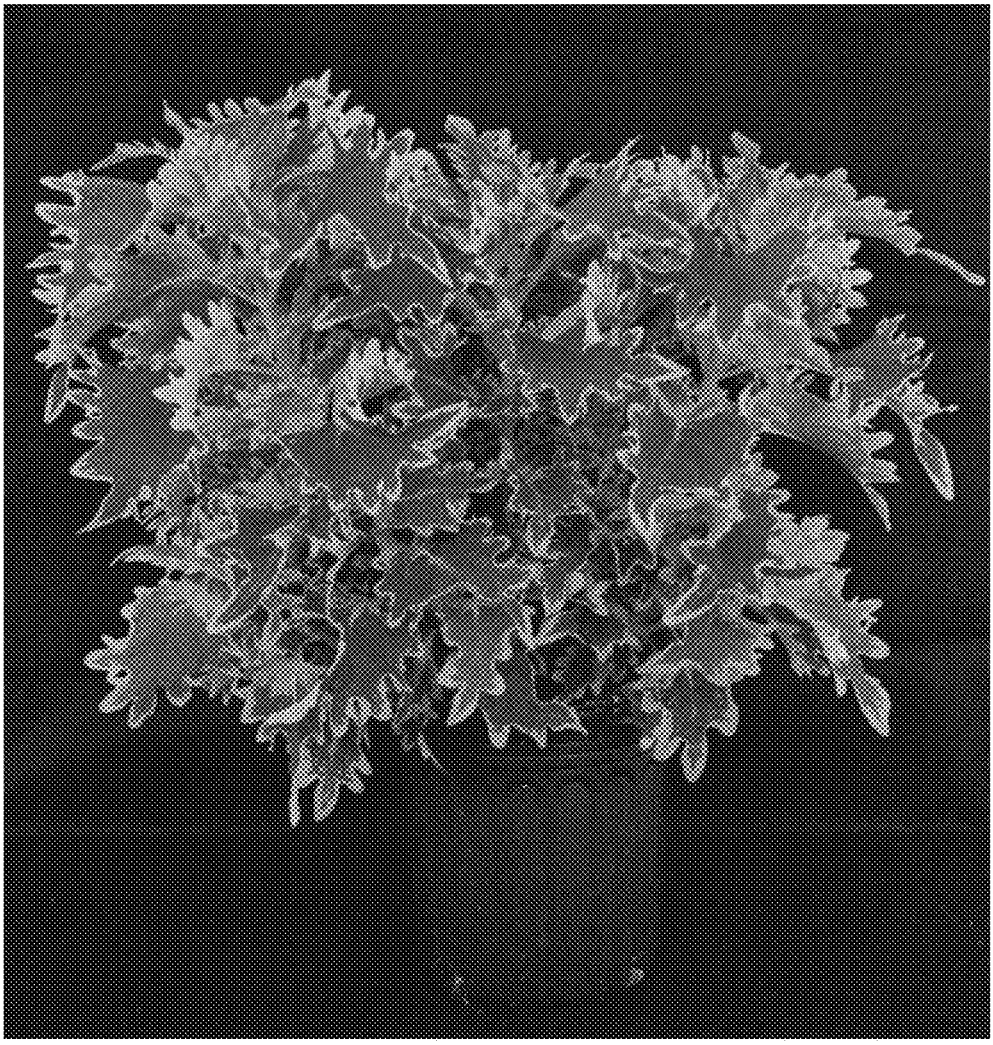
FIGS. 2 and 3 were taken from plants grown nine (9) weeks from unrooted cuttings in September-November 2020 in a glass-covered greenhouse in Gainesville, Fla.
Figure 3:
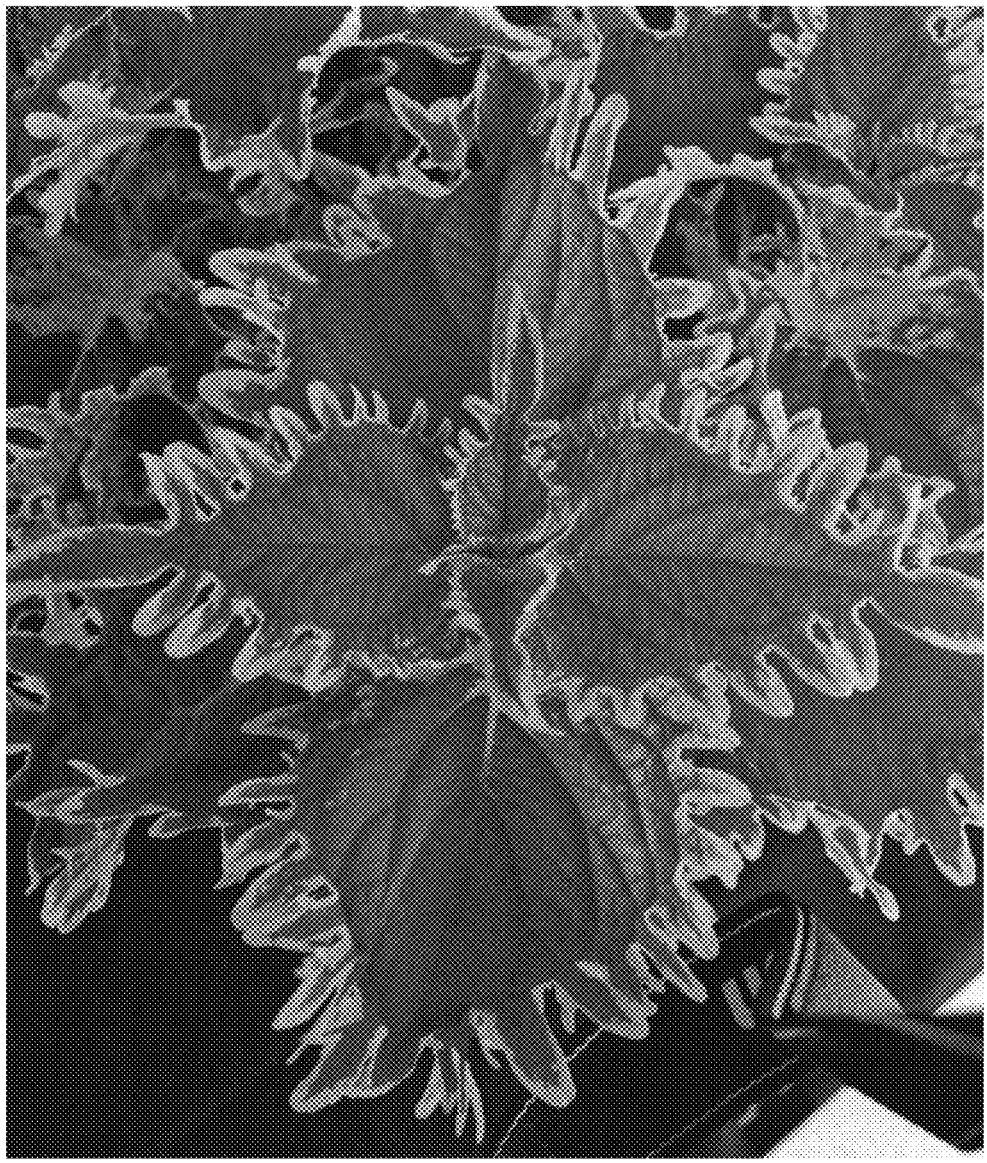

The following detailed description sets forth the distinctive characteristics of the new *Coleus* cultivar 'UF17-52-25'. Color references are made to The Royal Horticultural Society (R.H.S.) Colour Chart, 2007 ($5^{th}$ Edition).

DESCRIPTION OF GROWING CONDITIONS

The detailed description was obtained using nine-week-old plants grown from unrooted cuttings in September-November 2020 in a glass-covered greenhouse in Gainesville, Fla. The plants were propagated in mist for ten (10) days after cuttings were stuck, then grown in one-gallon pots for approximately seven and a half additional weeks.

BOTANICAL DESCRIPTION

Botanical classification:

*Family*.—Lamiaceae.

*Botanical name.*—*Coleus scutellarioides.*
*Common name.*—*Coleus.*
*Cultivar.*—'UF17-52-25'.

Parentage:
*Female or seed parent.*—'UF16-39-4'.
*Male or pollen parent.*—Unknown.

Propagation:
*Type cuttings.*—Vegetative meristems having at least one node.
*Time to initiate roots.*—3-4 days.
*Time to produce a rooted cutting.*—7-10 days.

Root description: Callus forms in 2-3 days, roots initiate in 3-4 days, and roots become a highly branched cutting in 7-10 days.
*Rooting habit.*—Fibrous.

Plant description:
*Plant form.*—Compact.
*Growth habit.*—Upright, well-branched.
*Plant height* (*from top of soil*).—28-32 cm.
*Plant width* (*horizontal plant diameter*).—50-55 cm.
*Branches.*—Quantity per plant: 7-8. Branch color: RHS 143C (light green). Texture: Smooth. Pubescence: Not present. Branch diameter: 0.5-0.7 cm at the base of a 28-cm-long branch. Branch length: 24-26 cm. Internode length: 2-3 cm. Anthocyanin: Not present. Stem description: Square-shaped stem, 0.9 cm in diameter at the soil line.

Foliage description:
*Quantity of leaves per branch.*—20-22. Arrangement: Opposite.
*Fragrance.*—Not fragrant.
*Shape.*—Ovate.
*Length.*—10-12 cm.
*Width.*—8-10 cm.
*Apex.*—Broadly acute.
*Base.*—Attenuate.
*Margin.*—Deeply lobed.
*Leaf texture* (*both surfaces*).—Smooth.
*Pubescence* (*both surfaces*).—Not present.
*Venation color.*—Upper surface: Proximal (base): RHS 142C (light green). Distal (tip): RHS 60C (deep red purple). Center: RHS 60C (deep red purple); midveins become RHS 61D (pink) as leaves mature. Lower surface: RHS 142C (light green).
*Venation pattern.*—Upper surface: Reticulate. Lower surface: Reticulate.
*Color, immature leaf.*—Upper surface: Base: RHS N170A (medium brown). Center: RHS 63C (medium pink). Margin: RHS N144C (light green). Lower surface: RHS 141D (light green).
*Color, mature leaf.*—Upper surface: Base: RHS N170A (medium brown). Center: RHS 64C (strong purple red). Margin: RHS N144C (light green). Lower surface: Base: RHS 141D (light green). Center: RHS 64A (dark purple). Margin: RHS 141C (medium green).
*Petiole length.*—2-3 cm.
*Petiole diameter.*—0.2-0.3 cm.
*Petiole color.*—RHS 142A (light green).
*Petiole texture.*—Smooth, no pubescence.

Flowers and seeds: Flowers and seeds have not been observed.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Peronospora lamii*). This pathogen has been observed in stock materials grown closely together in cooler growing seasons.

COMPARISON WITH KNOWN CULTIVARS

Plants of the new *Coleus* cultivar 'UF17-52-25' can be compared to those of 'UF16-45-18' (commercial name Stained Glassworks Crown Jewel, not patented). The color of the adaxial surface of mature leaves of 'UF17-52-25' is RHS N170A (medium brown) at the leaf base and RHS 64C (strong purple red) in the leaf center, with leaf margins and tip accents colored RHS N144C (light green). In contrast, the color of the adaxial surface of mature leaves of 'UF16-45-18' is RHS 183A (dark red) in the center and most of the leaf with leaf margins colored RHS 151C (green yellow).

Plants of the new *Coleus* cultivar 'UF17-52-25' can be compared to those of 'UF18-62-10' (patent applied for, U.S. application Ser. No. 17/300,456). The upper surfaces of mature leaves of 'UF17-52-25' are medium brown (RHS N170A) with a strong purple red (RHS 64C) center and light green margins (RHS N144C), whereas the upper surfaces of mature leaves of 'UF18-62-10' are dark red (RHS 183A) with a red-purple (RHS 63B) center and light green margins (RHS N144C). Also, leaves of 'UF17-52-25' are smaller than leaves of 'UF18-62-10'.

What is claimed is:

1. A new and distinct *Coleus scutellarioides* plant named 'UF17-52-25' as shown and described herein.

* * * * *